US010010353B2

(12) United States Patent
Biedermann et al.

(10) Patent No.: US 10,010,353 B2
(45) Date of Patent: Jul. 3, 2018

(54) POLYAXIAL BONE ANCHORING DEVICE

(71) Applicant: Biedermann Technologies GmbH & Co. KG, Donaueschingen (DE)

(72) Inventors: Lutz Biedermann, VS-Villingen (DE); Bernd Fischer, Braeunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 55 days.

(21) Appl. No.: 15/299,390

(22) Filed: Oct. 20, 2016

(65) Prior Publication Data

US 2017/0128102 A1 May 11, 2017

Related U.S. Application Data

(63) Continuation of application No. 13/914,535, filed on Jun. 10, 2013, now Pat. No. 9,498,253.
(Continued)

(30) Foreign Application Priority Data

Jun. 11, 2012 (EP) .................................. 12171525

(51) Int. Cl.
*A61B 17/70* (2006.01)
(52) U.S. Cl.
CPC ...... *A61B 17/7032* (2013.01); *A61B 17/7035* (2013.01); *A61B 17/7037* (2013.01)
(58) Field of Classification Search
CPC ............ A61B 17/7032; A61B 17/7034; A61B 17/7035; A61B 17/7037; A61B 17/7038
(Continued)

(56) References Cited

U.S. PATENT DOCUMENTS 7,922,748 B2 4/2011 Hoffman
7,972,364 B2 7/2011 Biedermann et al.
(Continued)

FOREIGN PATENT DOCUMENTS

EP 0 221 012 A1 5/1987
EP 1 323 391 A2 7/2003
(Continued)

OTHER PUBLICATIONS

Office action for U.S. Appl. No. 13/944,328, dated Mar. 25, 2014, 16 pages.
(Continued)

*Primary Examiner* — Ellen C Hammond
*Assistant Examiner* — Christina Negrellirodrigue
(74) *Attorney, Agent, or Firm* — Lewis Roca Rothgerber Christie LLP

(57) ABSTRACT

A polyaxial bone anchoring device is provided comprising a bone anchoring element having a shank to be anchored in a bone and a head; a receiving part coupled to the shank and configured to pivotably receive the head, and having a channel for receiving a rod and a longitudinal axis; a pressure member configured to be positioned in the receiving part; a locking member insertable into the channel; wherein the pressure member has a deformable portion; and wherein, when the locking member is advanced into the channel in the direction of the longitudinal axis, the locking member in moveable from a position where it contacts the pressure member resulting in a load applied to the pressure member that clamps the head, to a position where the locking member contacts the pressure member such that the deformable portion is deformed and the locking member contacts the rod and clamps the rod.

19 Claims, 5 Drawing Sheets

Related U.S. Application Data

(60) Provisional application No. 61/658,120, filed on Jun. 11, 2012.

(58) Field of Classification Search
USPC .................................. 606/264–278, 300–321
See application file for complete search history.

(56) References Cited

U.S. PATENT DOCUMENTS

| | | | |
|---|---|---|---|
| 8,016,862 B2* | 9/2011 | Felix | A61B 17/7032 606/266 |
| 8,088,152 B2 | 1/2012 | Schumacher | |
| 8,167,910 B2 | 5/2012 | Nilsson | |
| 8,998,959 B2 | 4/2015 | Jackson | |
| 9,241,737 B2 | 1/2016 | Biedermann et al. | |
| 2003/0100896 A1 | 5/2003 | Biedermann et al. | |
| 2003/0125741 A1 | 7/2003 | Biedermann et al. | |
| 2003/0167058 A1 | 9/2003 | Shluzas | |
| 2004/0193160 A1 | 9/2004 | Richelsoph | |
| 2005/0277928 A1 | 12/2005 | Boschert | |
| 2006/0149241 A1 | 7/2006 | Richelsoph et al. | |
| 2006/0200131 A1 | 9/2006 | Chao et al. | |
| 2006/0276792 A1 | 12/2006 | Ensign et al. | |
| 2007/0118123 A1 | 5/2007 | Strausbaugh et al. | |
| 2007/0123862 A1 | 5/2007 | Warnick | |
| 2008/0045953 A1 | 2/2008 | Garamszegi | |
| 2008/0161859 A1 | 7/2008 | Nilsson | |
| 2008/0188898 A1 | 8/2008 | Jackson | |
| 2008/0294202 A1 | 11/2008 | Peterson et al. | |
| 2009/0105770 A1 | 4/2009 | Berrevoets et al. | |
| 2009/0254125 A1 | 10/2009 | Predick | |
| 2010/0125302 A1 | 5/2010 | Hammill, Sr. et al. | |
| 2010/0160977 A1 | 6/2010 | Gephart et al. | |
| 2010/0160980 A1 | 6/2010 | Walsh et al. | |
| 2010/0160981 A1 | 6/2010 | Butler et al. | |
| 2010/0234902 A1 | 9/2010 | Biedermann et al. | |
| 2010/0241175 A1 | 9/2010 | Walker et al. | |
| 2010/0298891 A1 | 11/2010 | Jackson | |
| 2011/0098755 A1 | 4/2011 | Jackson et al. | |
| 2011/0282399 A1 | 11/2011 | Jackson | |
| 2012/0041490 A1 | 2/2012 | Jacob et al. | |
| 2012/0078307 A1 | 3/2012 | Nihalani | |
| 2012/0124813 A1 | 5/2012 | Biedermann et al. | |
| 2012/0143266 A1 | 6/2012 | Jackson et al. | |
| 2012/0253408 A1 | 10/2012 | Timm | |
| 2013/0018428 A1* | 1/2013 | Harper | A61B 17/7056 606/305 |
| 2015/0032162 A1 | 1/2015 | Biedermann et al. | |
| 2016/0038204 A1 | 2/2016 | Biedermann et al. | |

FOREIGN PATENT DOCUMENTS

| | | |
|---|---|---|
| EP | 1743584 A1 | 1/2007 |
| EP | 2286748 A1 | 2/2011 |
| EP | 2 457 527 A1 | 5/2012 |
| EP | 2 687 172 A1 | 1/2014 |
| WO | WO 2006/116437 A2 | 11/2006 |
| WO | WO 2008/103150 A1 | 8/2008 |
| WO | WO 2009/038697 A1 | 3/2009 |
| WO | WO 2012/064360 A1 | 5/2012 |
| WO | WO 2012/091737 A1 | 7/2012 |

OTHER PUBLICATIONS

Final Office action for U.S. Appl. No. 13/944,328, dated Jul. 22, 2014, 18 pages.
Office action for U.S. Appl. No. 13/944,328, dated Mar. 23, 2015, 16 pages.
Office action for U.S. Appl. No. 14/339,304, dated Oct. 15, 2015, 15 pages.
European Search Report and Opinion issued by the EPO for EP 12171525.4 dated Nov. 2, 2012 (7 pages).

\* cited by examiner

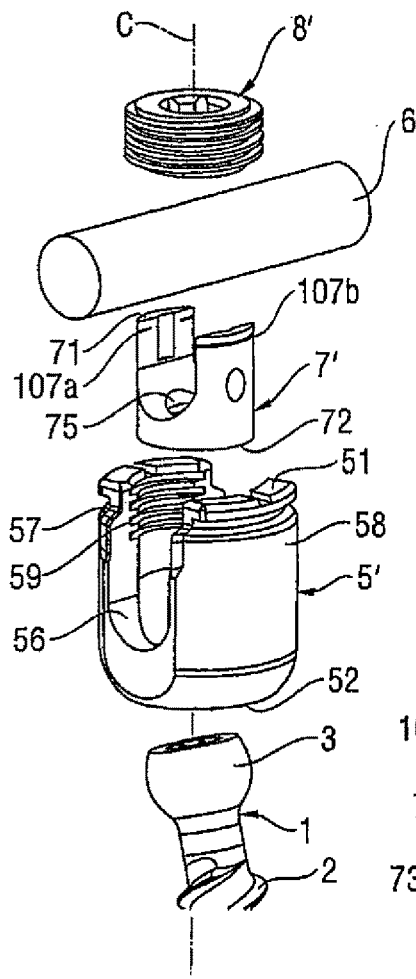
Fig. 12
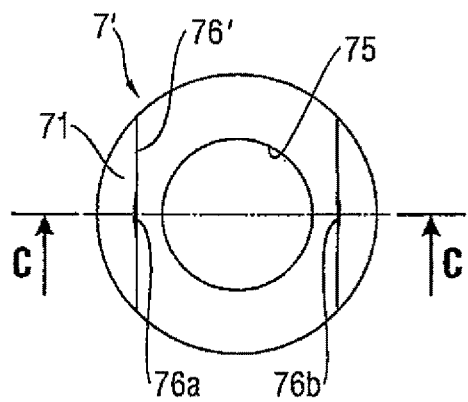
Fig. 13
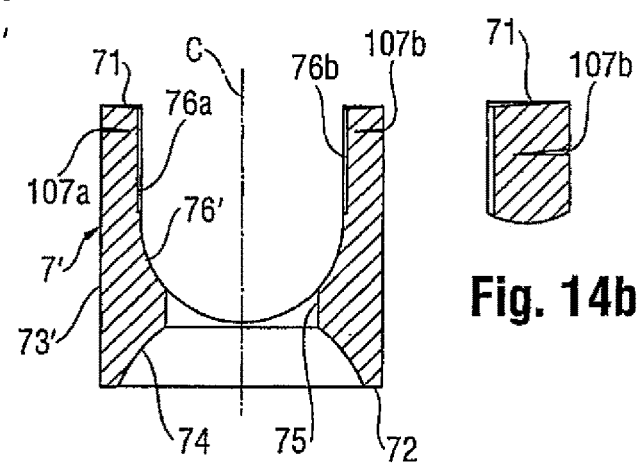
Fig. 14a
Fig. 14b
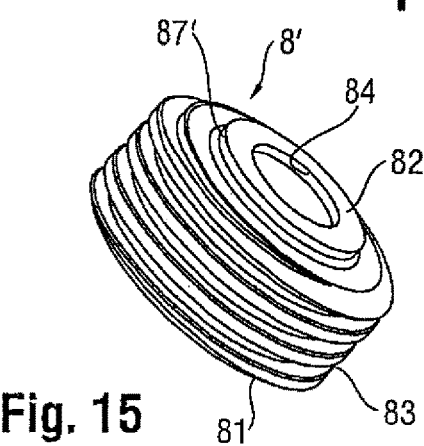
Fig. 15
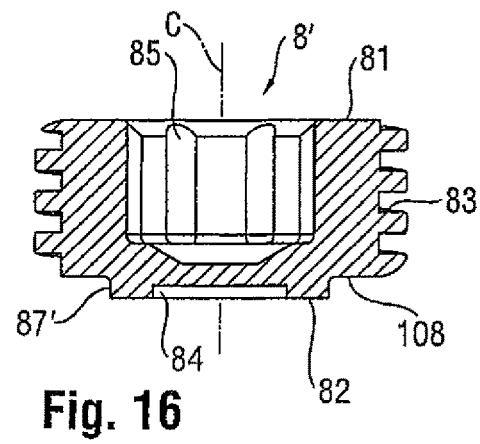
Fig. 16

POLYAXIAL BONE ANCHORING DEVICE

CROSS-REFERENCE TO RELATED APPLICATIONS

This application is a continuation of U.S. patent application Ser. No. 13/914,535, filed Jun. 10, 2013, which claims the benefit of U.S. Provisional Patent Application Ser. No. 61/658,120, filed Jun. 11, 2012, the contents of which are hereby incorporated by reference in their entirety, and which claims priority from European Patent Application EP 12 171 525.4, filed Jun. 11, 2012, the contents of which are hereby incorporated by reference in their entirety.

BACKGROUND

Field of the Invention

The invention relates to a polyaxial bone anchoring device, in particular for use in spinal or trauma surgery. The polyaxial bone anchoring device comprises a bone anchoring element with a shank to be anchored in a bone and a head. The head is pivotably held in a receiving part and can be fixed at an angle by applying pressure onto it via a pressure member. With the receiving part, the bone anchoring element can be coupled to a stabilization rod that is placed into a channel of the receiving part and that can be secured by a locking member. The pressure member comprises a deformable portion. When the locking member is advanced into the channel, first, the locking member contacts the pressure member resulting in a load applied to the pressure member that clamps the head and thereafter the locking member contacts the pressure member such that the deformable portion is deformed and the locking member comes into contact with the rod and clamps the rod. With such a locking member the head and the rod can be fixed in a sequential manner using a tool with a single drive portion that engages the locking member.

Description of Related Art

US 2003/0100896 A1 describes a polyaxial bone anchoring device wherein in one embodiment a single piece locking element is used to lock the head and the rod simultaneously when the locking element is tightened.

U.S. Pat. No. 7,972,364 describes a locking assembly for securing a rod in a rod receiving part of a bone anchoring device that includes a first locking element and a second locking element. With the first locking element and the second locking element the head of the bone anchoring element and the rod can be locked independently using a tool with two drive portions.

U.S. Pat. No. 8,088,152 B2 describes an orthopedic retaining system comprising at least one bone screw which has a head part and a threaded shaft pivotably mounted thereon. A clamping element is mounted in the head part, which can be pressed against the threaded shaft from its upper side and, as a result, secure the threaded shaft relative to the head part. A retaining bar is arranged in a receptacle of the head part. Further, a clamping device is provided on the upper side of the head part, by means of which the clamping element and the retaining bar are pressed into the head part such that the threaded shaft and the retaining bar are secured in positions relative to the head part. The clamping device comprises an elastically deformable pressure element which is displaced into a clamping position during actuation of the clamping device. With such a configuration, upon actuation of the clamping device, the pressure element abuts first on the clamping element and thereby secures the pivotable threaded shaft in position on the head part while the retaining bar remains freely displaceable. Only upon further actuation of the clamping device the pressure element is elastically deformed thereby abutting on the retaining bar and securing the retaining bar in position.

SUMMARY

It is the object of the invention to provide an improved polyaxial bone anchoring device that provides for simplified handling and a reliable fixation of the head and the rod.

In an embodiment of the invention, the polyaxial bone anchoring device allows a surgeon to lock the head of the bone anchoring element in the receiving part and to lock the rod in a sequential manner using only a single tool with a single drive portion. By this sequential locking mechanism it is possible to first lock, or at least preliminarily clamp, the head and thereafter clamp the rod and finally lock the rod and the head. Moreover, a full locking of the head and the rod can be carried out and thereafter the fixation of the rod can be loosened to perform adjustments of the rod.

As discussed regarding the above embodiment, because only a single tool with a single drive portion and one-piece loading member is needed for performing these steps, the use of the polyaxial bone anchoring device is facilitated.

In one embodiment, the polyaxial bone anchoring device comprises only few parts. The pressure member and the locking member can be used with existing receiving parts. Hence, existing receiving parts may be upgraded with a sequential locking mechanism to allow an independent head and rod fixation. Thus, the number of parts of the polyaxial bone anchoring device that has the sequential locking mechanism is the same as the number of parts of a polyaxial bone anchoring device wherein the head and the rod are locked simultaneously.

The pressure member and the locking element are relatively easy to manufacture.

BRIEF DESCRIPTION OF THE DRAWINGS

Further features and advantages of the invention will become apparent from and will be best understood by reference to the following detailed description reviewed in conjunction with the accompanying drawings. In the drawings:

FIG. 5b shows an enlarged view of a portion of FIG. 5a.

FIG. 10b shows an enlarged view of a portion of FIG. 10a.

FIG. 11b shows an enlarged view of a portion of FIG. 11a.

FIG. 12 shows a perspective exploded view of the polyaxial bone anchoring device according to a second embodiment.

FIG. 13 shows a top view of the pressure member of the polyaxial bone anchoring device according to FIG. 12.

FIG. 14a shows a cross-sectional view of the pressure member of FIG. 13 along line C-C in FIG. 13.

FIG. 14b shows an enlarged view of a portion of FIG. 13.

FIG. 15 shows a perspective view from the bottom of the locking member of the polyaxial bone anchoring device according to the second embodiment.

FIG. 16 shows a cross-sectional view of the locking member according to the second embodiment.

FIG. 18b shows an enlarged view of a portion of FIG. 18a.

DETAILED DESCRIPTION

Figures 1, 2:
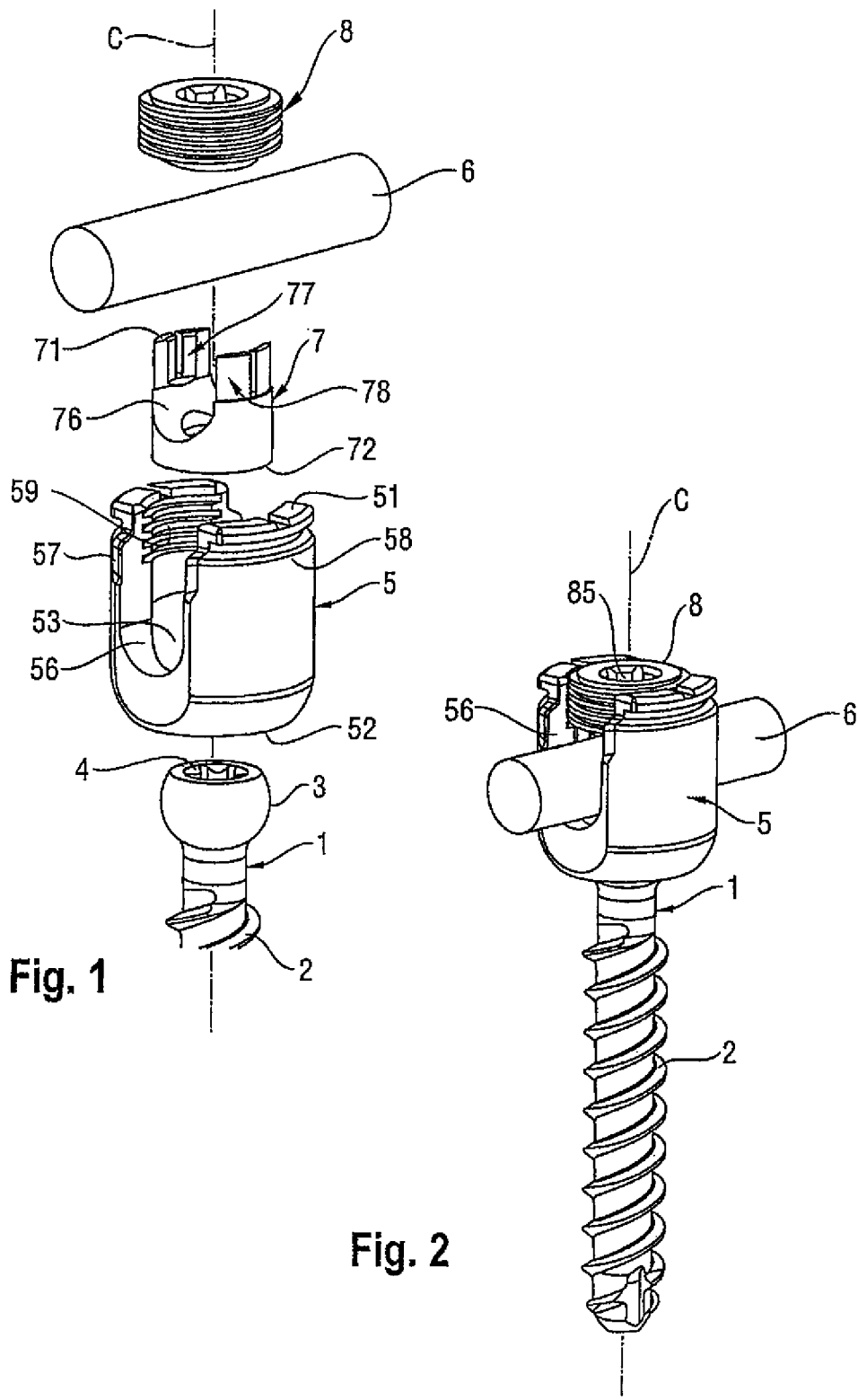
FIG. 1 shows a perspective exploded view of the polyaxial bone anchoring device according to a first embodiment.
FIG. 2 shows a perspective view of the polyaxial bone anchoring device according to the first embodiment in an assembled state.
Figure 3:
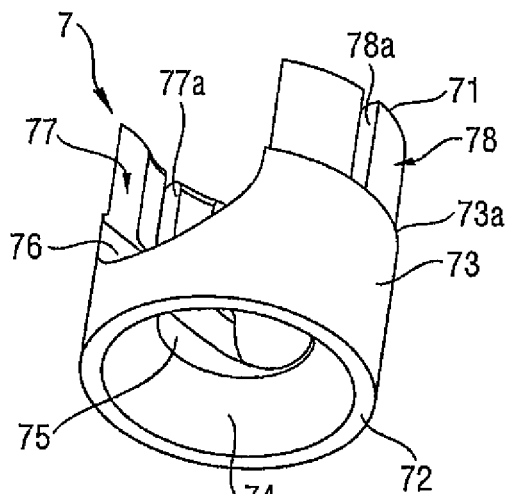
FIG. 3 shows a perspective view from the bottom of the pressure member of the polyaxial bone anchoring device according to the first embodiment.
Figure 4:
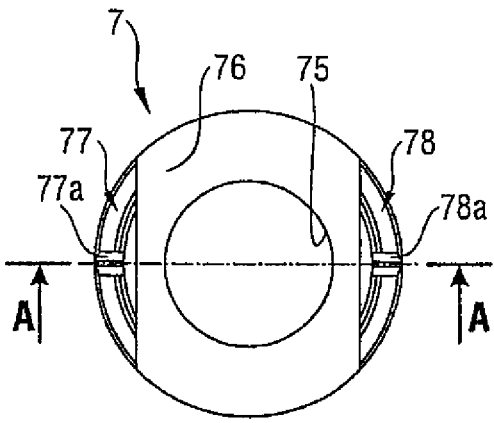
FIG. 4 shows a top view of the pressure member shown in FIG. 3.
Figure 5A:
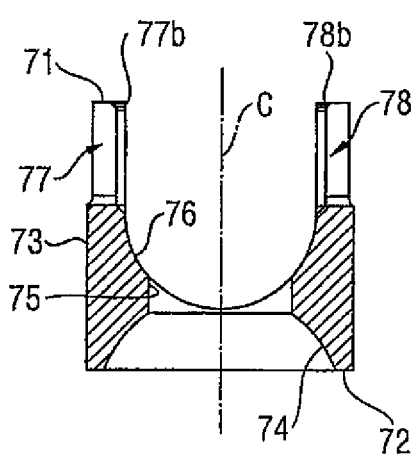
FIG. 5a shows a cross-sectional view of the pressure member, the section taken along line A-A in FIG. 4.
Figure 5B:
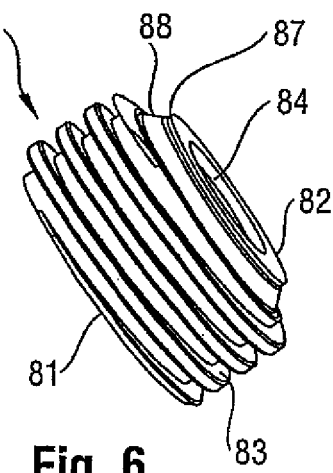
Figure 6:
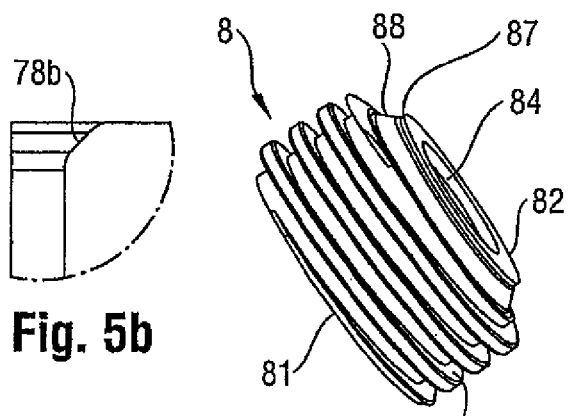
FIG. 6 shows a perspective view from one side of the locking member of the polyaxial bone anchoring device according to the first embodiment.
Figure 7:
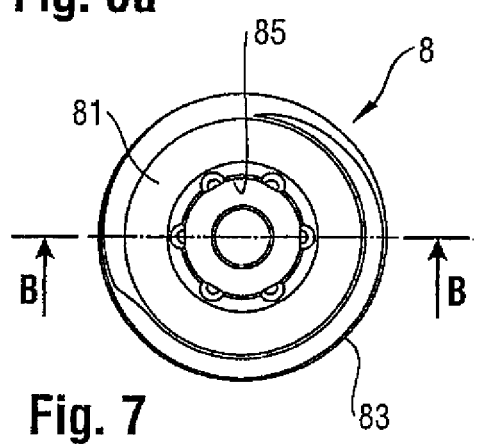
FIG. 7 shows a top view of the locking member of FIG. 6.
Figure 8:
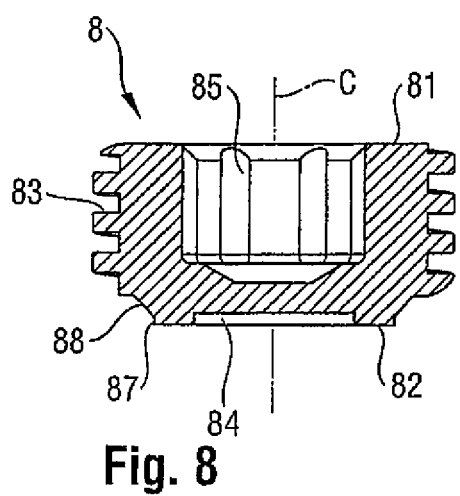
FIG. 8 shows a cross-sectional view of the locking member, the section being taken along line B-B in FIG. 7.

A polyaxial bone anchoring device according to a first embodiment is shown in FIGS. 1 and 2. It comprises an anchoring element 1 having a shank 2 with a threaded portion and a head 3. The head 3 has a spherically-shaped outer surface portion and, on its side opposite to the shank 2, a recess 4 for engagement with a tool. A receiving part 5 is provided for coupling the bone anchoring element 1 to a rod 6. In the receiving part 5, a pressure member 7 is arranged to exert pressure onto the head 3 of the bone anchoring element 1.

Referring to FIGS. 1 and 2 as well as FIGS. 9 to 12, the receiving part 5 has a top end 51 and a bottom end 52 and is of substantially cylindrical construction with a longitudinal axis C extending through the top end 51 and the bottom end 52. Coaxially with the longitudinal axis C, a bore 53 is provided extending from the top end 51 to a predetermined distance from the bottom end 52. At the bottom end 52, an opening 54 is provided, the diameter of which is smaller than the diameter of the bore 53. The coaxial bore 53 narrows towards the opening 54, for example, with a spherically-shaped section 55 that provides a seat for the head 3. However, the section 55 can have any other shape such as, for example, a conical shape, that ensures the function of the head 3 being pivotably held in the receiving part 5 similar to a ball and socket joint.

The receiving part 5 further comprises a U-shaped recess 56 starting at the top end 51 and extending in the direction of the bottom end 52. By means of the U-shaped recess 56, two free legs 57, 58 are formed that extend towards the top end 51 and define a channel for receiving the rod 6. Adjacent to the top end 51, a portion with an internal thread 59 is provided at the inner surface of the legs 57, 58. In the embodiment shown, the internal thread 59 is a flat thread having substantially horizontal upper and lower thread flanks. Any other thread form can be used for the internal thread 59, however, a thread form that reduces or eliminates splaying of the legs is preferable. Below the portion with the internal thread 59 the bore 53 comprises a slightly enlarged portion 53a which provides space for the expansion of a portion of the pressure member 7 described below.

As shown in FIG. 1 and FIGS. 3 to 5, the pressure member 7 is of a substantially cylindrical construction with a top end 71 and a bottom end 72 and a cylinder axis C extending through the two ends 71, 72 and when the pressure member 7 is in a mounted state, the cylinder axis C is the same as or coaxial with the longitudinal axis C of the receiving part 5.

The pressure member 7 is arranged in the receiving part 5 such that its top end 71 is oriented towards the top end 51 of the receiving part 5 and the bottom end 72 is oriented towards the bottom end 52 of the receiving part 5. The pressure member 7 comprises a first cylindrical portion 73 adjacent the bottom end 72 with an outer diameter that is slightly smaller than the inner diameter of the bore 53 of the receiving part 5 so that the pressure member 7 can be introduced into the receiving part 5 from the top end 51 thereof. Adjacent to the bottom end 72, a spherically-shaped recess 74 is provided that cooperates with a spherical outer surface portion of the head 3 of the bone anchoring element 1. A coaxial through-hole 75 extends through the pressure member 7 that allows access to the screw head 3 with a tool (not shown). The end of the cylindrical portion 73 opposite to the bottom end 72 has a rim 73a from which a substantially cylindrically-shaped recess 76 extends in the direction of the bottom end 72. The dimensions of the recess 76 are such that the rod 6 can be inserted and guided therein.

Two upstanding walls 77, 78 are provided on the rim 73a, the free ends of which form the top end 71 of the pressure member 7. The walls 77, 78 have a height such that together with the recess 76 they form a channel for inserting the rod 6, wherein the depth of the channel is greater than the diameter of the rod 6. Hence, when the rod 6 is inserted, the top end 71 of the pressure member 7 extends above an upper surface of the rod 6. The walls 77, 78 are substantially cylindrically-shaped with the cylinder axis being the cylinder axis C of the pressure member 7. Each wall 77, 78 is divided by a longitudinal slit 77a, 78a that is substantially parallel to the cylinder axis C. The outer diameter of the pressure member 7 in the area of the walls 77, 78 is slightly smaller than the outer diameter of the pressure member 7 at the cylindrical portion 73. Hence, when the pressure member 7 is inserted into the bore 53 of the receiving part 5 and the walls 77, 78 are located in the section 53a of the bore 53, there is a gap 79 between the inner wall of the bore section 53a and the walls 77, 78, as shown in FIGS. 9 to 11b. The slits 77a, 78a render the walls 77, 78 elastically deformable with respect to the cylindrical portion 73 of the pressure member 7. This means, that the walls 77, 78 can be bent radially outward and return elastically to their upright position. Hence, the walls 77, 78 form a deformable portion of the pressure member 7. Adjacent to the top end 71, the wall portions 77, 78 comprise inclined inner edges 77b, 78b that provides an abutment for a locking member 8, which is described below. The incline may be, for example, around 45° with respect to the central axis C.

The locking member 8 will be described with reference to FIGS. 1 and 6 to 8. The locking member 8 is a monolithic piece. In the embodiment shown, it is a set screw. The locking member has a top end 81 and a bottom end 82 that faces the pressure member 7 when the locking member 8 is inserted between the legs 57, 58 of the receiving part 5. An external thread 83 of the locking member 8 cooperates with the internal thread 59 of the receiving part 5. A coaxial recess 84 is provided at the bottom end 82. It shall be mentioned, that the recess 84 can be omitted and/or a coaxial through hole can be provided. Adjacent the top end 81, there is an engagement portion 85 for a tool, which may be, for example, formed as a recess with longitudinal grooves, as a hexagon or other polygon recess, torx-shaped recess or may have any other shape making it suitable as an engagement portion. Hence, with the engagement portion 85, the locking member 8 has a single drive portion for a drive tool.

Adjacent the bottom end 82, there is a cylindrical portion 87 with an outer diameter that is only slightly smaller than the inner diameter of the pressure member 7 between the walls 77, 78 so that the cylindrical portion 87 may extend between the walls 77, 78. Between the cylindrical portion 87 and the external thread 83, there is a conical portion 88 with a cone angle selected such that it corresponds to the angle of inclination of the inclined edges 77*b*, 78*b* of the walls 77, 78. The size of the conical portion 88 in an axial direction is greater than the size of the inclined edges 77*b*, 78*b* of the wall portions 77, 78, so that when the conical portion 88 comes into engagement with the inclined edges 77*b*, 78*b*, a movement of the locking member 8 towards the pressure member 7 keeps the inclined edges 77*b*, 78*b* and the conical portion 88 in contact over a certain length.

The parts of the bone anchoring device are made of a bio-compatible material, for example, of a bio-compatible metal or a metal alloy, such as titanium, stainless steel, nickel titanium alloys, such as Nitinol, or made of a bio-compatible plastic material, such as for example PEEK (polyetheretherketone). The parts can be made all of the same or of different materials.

In use, the receiving part 5 and the anchoring element 1 as well as the pressure member 7 are normally pre-assembled such that the head 3 is pivotably held in the seat 55 of the receiving part 5 and the pressure member 7 is placed onto the head 3. Usually, at least two polyaxial bone anchoring devices shall be connected via the rod 6. After insertion of the bone anchoring elements 1 into the bone, the receiving parts 5 are aligned by pivoting the receiving parts 5 relative to the heads 3 and then the rod 6 is inserted.

Figure 9:
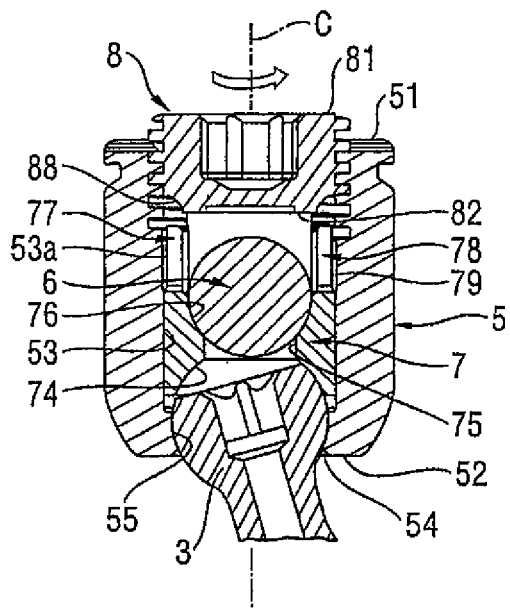
FIG. 9 shows a cross-sectional view of the polyaxial bone anchoring device according to the first embodiment with a rod inserted, wherein the section is taken in a plane perpendicular to the rod axis in a first configuration of the locking member.
Figure 10A:
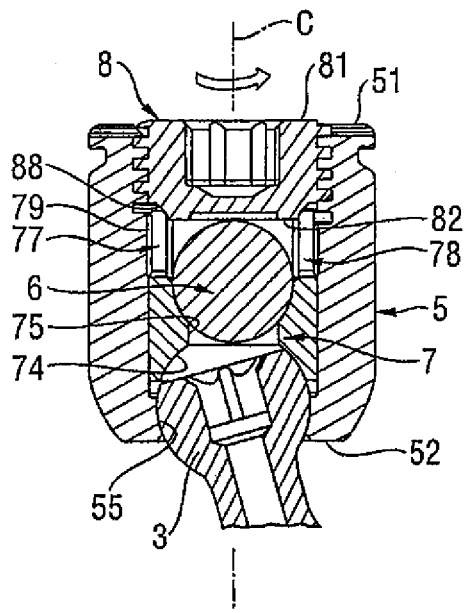
FIG. 10a shows a cross-sectional view of the polyaxial bone anchoring device as in FIG. 9, wherein the locking member is in a second configuration.
Figure 10B:
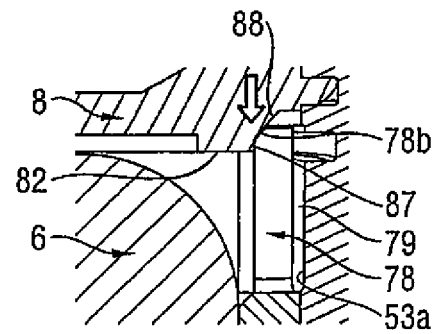

The locking procedure will be explained with reference to FIGS. 9 to 11*b*. First, as shown in FIG. 9, the locking member 8 is inserted into the receiving part 5 with the bottom end 82 of the locking member facing the rod 6. The locking member 8 is then further screwed-in until its cylindrical portion 87 extends into the space between the walls 77, 78 and the conical portion 88 of the locking member 8 abuts against the inclined edges 77*b*, 78*b* of the walls 77, 78. Further advancement of the locking member 8 into the receiving part 5 presses the pressure member 7 against the head 3 as shown in FIGS. 10*a* and 10*b*. By means of this, the head 3 is clamped in an adjustable angular position with respect to the receiving part 5 and is held in this position by means of friction. The head 3 may be only slightly clamped or nearly completely locked.

Figure 11A:
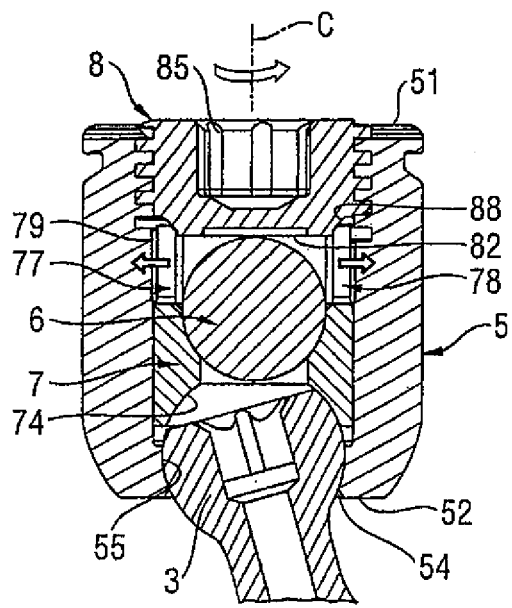
FIG. 11a shows a cross-sectional view of the polyaxial bone anchoring device as in FIG. 9 with the locking member in a third configuration.
Figure 11B:
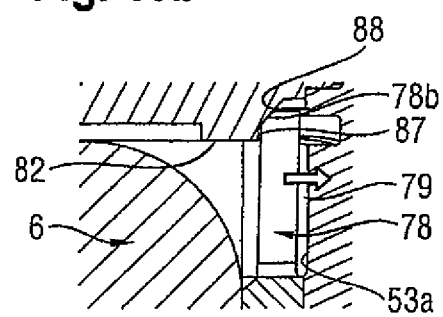

Then, as shown in FIGS. 11*a* and 11*b*, the further advancement of the locking member 8 results in a counterforce that the locking member 8 experiences from the pressure member 7. The walls 77, 78 are bent radially outward when the conical portion 88 presses onto the inclined edges 77*b*, 78*b* thereby moving the walls 77, 78 into the gap 79 that is present between the wall portions 77, 78 and the inner wall of the bore section 53*a* (see arrows in FIGS. 11*a* and 11*b*). This allows the bottom end 82 of the locking member 8 to move deeper into the channel where the rod 6 is seated and finally contact and lock the rod 6. By this procedure, the whole polyaxial bone anchoring device is locked.

It is possible to correct the position of the rod 6 without loosening the locking of the head 3. To achieve this, the locking member 8 is screwed-back until the rod 6 becomes displaceable. This is possible due to the resilient property of the deformable walls 77, 78 of the pressure member 7. It may even be possible to fully remove the locking member 8 and to carry out a complete revision of the locking of the polyaxial bone anchoring device.

A second embodiment of the polyaxial bone anchoring device will be described with reference to FIGS. 12 to 18*b*. The second embodiment differs from the first embodiment in the design of the pressure member and of the locking member. Parts and portions that are identical to the first embodiment have the same reference numerals and the description thereof will not be repeated.

The pressure member 7' has a top end 71 and a bottom end 72 and a substantially cylindrical portion 73' that extends from the top end 71 to the bottom end 72.

A U-shaped recess 76' extends from the top end 71 to a distance from the bottom end 72. The depth of the U-shaped recess 76' is greater than the diameter of the rod 6 so that when the rod 6 is inserted, the top end 71 of the pressure member 7' extends above an upper surface of the rod 6. Small coaxial cylindrical recesses 76*a*, 76*b* extends from the top end 71 into the sidewalls of the channel formed by the U-shaped recess 76'. The recesses 76*a*, 76*b* contribute to rendering the upper portion of the pressure member 7' deformable. At a distance from the top end 71 of both sidewalls, a notch 107*a*, 107*b* in the outer surface extending in a transverse or circumferential direction relative to the central axis C is provided. The contours of the notches 107*a*, 107*b* are substantially V-shaped, i.e. the widths of the notches 107*a*, 107*b* are increasing towards the outer surface of the sidewalls. This renders the upper portion of the pressure member 7' elastically deformable in such a way that compressing the sidewalls of the pressure member 7' in an axial direction leads to a reduction of the height of the sidewalls.

The locking member 8' according to the second embodiment differs from the locking member 8 of the first embodiment in that it comprises only a cylindrical projection 87' that projects away from the threaded portion 83. The cylindrical projection 87' has a smaller diameter than the threaded portion 83 of the locking member, such that at the end of the threaded portion 83 a ring-shaped abutment 108 is formed that comes into contact with the top end 71 of the pressure member 7.

Figure 17:
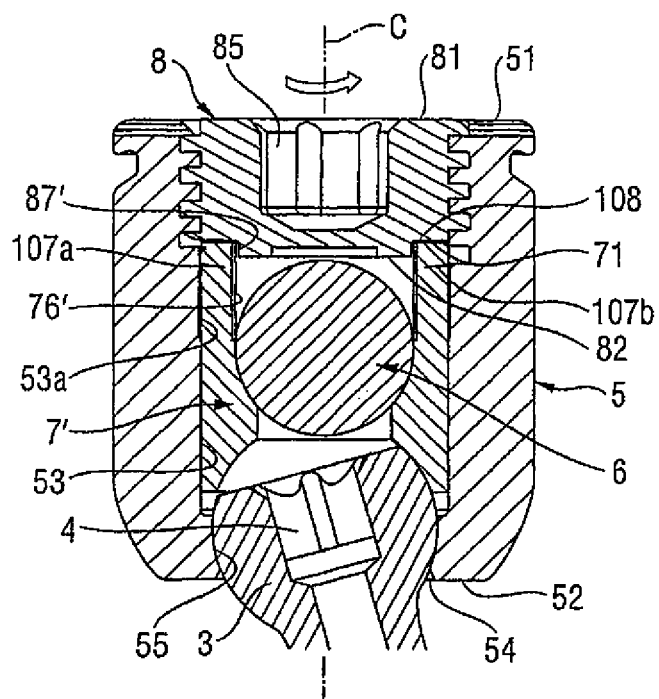
FIG. 17 shows a cross-sectional view of the polyaxial bone anchoring device according to the second embodiment with the rod inserted, wherein the section is taken in a plane perpendicular to the rod axis and the locking member is in a first configuration.
Figure 18A:
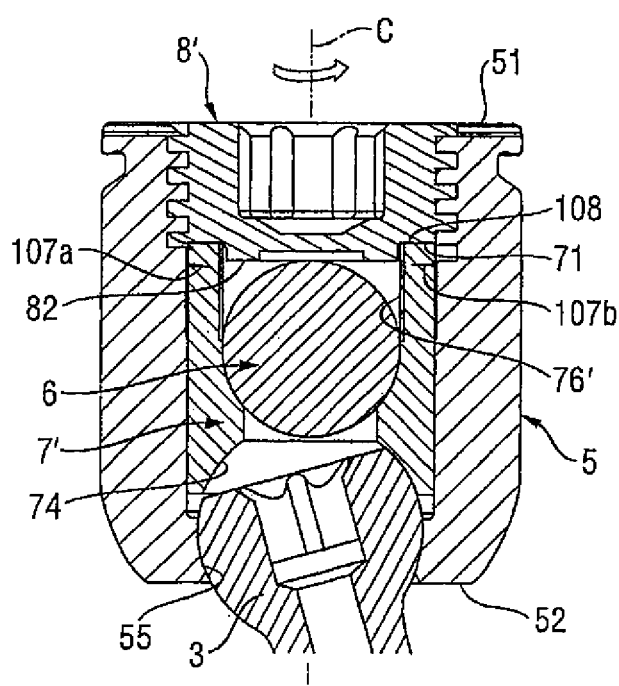
FIG. 18a shows a cross-sectional view of the polyaxial bone anchoring device according to the second embodiment with the locking member in a second configuration.
Figure 18B:
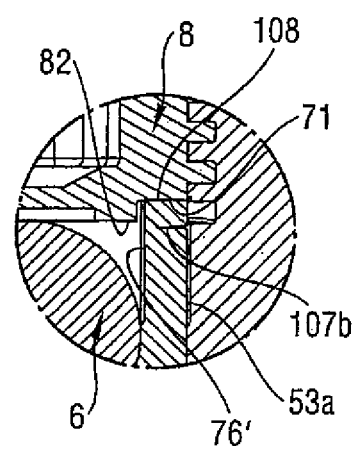

In use, as shown in FIG. 17, when the locking member 8' is inserted into the receiving part 5 and advanced towards the pressure member 7', the ring-shaped abutment 108 comes into contact with the top end 71 of the pressure member. Further advancement of the locking member 8' presses the pressure member 7' against the head 3 such that the head 3 is clamped by friction. Due to the counterforce experienced by the locking member 8' from the pressure member 7' when it presses the head 3 into the seat 55, the further advancement of the locking member 8 presses the abutment 108 against the top end 71 of the pressure member 7'. Thereby, the deformable portions formed by the notches 107*a*, 107*b* are deformed and the notches 107*a*, 107*b* are narrowed. Hence, the cylindrical portion 87' of the locking member 8' comes into contact with the surface of the rod 6 and presses onto the rod 6 to fix the rod 6.

For a correction of the position of the rod 6, the locking member 8' can be screwed-back slightly to render the rod 6 displaceable again. Because of the spring function of the deformable portion of the pressure member 7', the pressure on the head 3 that holds the head 3 in position is still present and the head remains clamped. Final tightening of the locking member 8' locks the whole assembly.

Various modifications of the previous embodiments are conceivable. In particular, the deformable portion can be realized also by resilient elements that are mounted onto the upper end of a pressure member. In such a case, the clamping force can be adjusted by selecting an element with a specific spring force. In addition, features of the different embodiments described can be combined among each other.

For the polyaxial bone anchoring device any known polyaxial bone anchoring devices can be used that comprise a bone anchoring element that is pivotably received in the receiving part. In particular, bone anchoring devices, wherein the bone anchoring element is introduced from the bottom end of the receiving part into the receiving part, may be used. The head does not need to have a spherical shape. It can also have flattened portions that may be used for restricting the pivoting movement to a single plane. The receiving part may be formed differently, in particular, inside. It can also have an inclined lower edge to allow an enlarged pivot angle to a specific direction. For the bone anchoring element, any known bone anchors, such as screws, nails, with or without cannulation, can be used.

The connection between the locking member and the receiving part does not necessarily have to be a threaded connection, other connections may be possible, such as for example, a bayonet connection.

The invention claimed is:

1. A polyaxial bone anchoring device comprising:
   a bone anchoring element having a shank to be anchored to a bone and a head;
   a receiving part configured to be coupled to the shank and to pivotably receive the head, the receiving part having a central axis and a channel for receiving a rod;
   a pressure member configured to be positioned in the receiving part and to exert pressure onto the head to lock the head in the receiving part, the pressure member having a top end, a bottom end, an annular portion, and a recess that extends from the top end towards the bottom end and that forms two sidewalls that meet at a bottom of the recess, wherein at least one of the sidewalls comprises an elastically deformable portion; and
   a locking member insertable into the channel, the locking member having a top end and a bottom end configured to face the pressure member;
   wherein when the head, the pressure member, and the locking member are in the receiving part, the locking member is movable in the channel of the receiving part along the central axis between a first position wherein the locking member contacts the pressure member and a load is applied to the head by the pressure member that clamps the head, and a second position wherein the locking member contacts the pressure member and deforms the elastically deformable portion to reduce a distance between the bottom end of the locking member and the bottom end of the pressure member, for the locking member to come into contact with the rod and lock the rod.

2. The polyaxial bone anchoring device of claim 1, wherein the elastically deformable portion located near the top end of the pressure member.

3. The polyaxial bone anchoring device of claim 1, wherein when the locking member is at the second position, the elastically deformable portion is deformed such that a portion of the corresponding sidewall near the top end of the pressure member bends radially outwardly from the central axis of the receiving part.

4. The polyaxial bone anchoring device of claim 1, wherein the sidewalls of the pressure member are configured to extend above the surface of the rod when the rod is seated in the recess, and wherein the elastically deformable portion is formed on each of the sidewalls.

5. The polyaxial bone anchoring device of claim 1, wherein the elastically deformable portion comprises at least one slit that extends in a direction substantially parallel to the central axis when the pressure member is in the receiving part, rendering the elastically deformable portion deformable.

6. The polyaxial bone anchoring device of claim 1, wherein the elastically deformable portion comprises at least one notch that extends in a direction substantially transverse to the central axis when the pressure member is in the receiving part.

7. The polyaxial bone anchoring device of claim 1, wherein the locking member comprises an inclined surface portion and the pressure member comprises a corresponding inclined surface portion configured to contact the inclined surface portion of the locking member, such that when the head, the pressure member, and the locking member are in the receiving part and the locking member is advanced towards the pressure member, an increasing force is generated on the pressure member that deforms the elastically deformable portion away from the central axis.

8. The polyaxial bone anchoring device of claim 1, wherein the elastically deformable portion deforms when the locking member presses against the elastically deformable portion, such that the distance in the axial direction between the locking member and the bottom of the recess of the pressure member is reduced.

9. The polyaxial bone anchoring device of claim 1, wherein the elastically deformable portion is monolithically formed with other portions of the pressure member.

10. The polyaxial bone anchoring device of claim 1, wherein the locking member is a single piece.

11. The polyaxial bone anchoring device of claim 1, wherein the locking member is a set screw.

12. The polyaxial bone anchoring device of claim 1, wherein the bottom end of the locking member comprises a surface portion that is configured to contact with the pressure member without the locking member contacting the rod.

13. The polyaxial bone anchoring device of claim 12, wherein the surface portion is ring-shaped.

14. The polyaxial bone anchoring device of claim 1, wherein the receiving part has a top end, a bottom end, and a bore extending from the top end to the bottom end, and wherein the channel for the rod is formed by a recess adjacent the top end with a substantially U-shaped cross-section.

15. The polyaxial bone anchoring device of claim 14, wherein two open legs are formed by the recess of the receiving part, and wherein an internal thread is provided at the legs that cooperates with an external thread of the locking member.

16. The polyaxial bone anchoring device of claim 1, wherein the elastically deformable portion is more deformable than portions of the sidewall positioned closer to the bottom end of the pressure member, and wherein when the head, the pressure member, and the locking member are in the receiving part and the locking member is at the first position, the entire elastically deformable portion is spaced apart from an inner wall of the receiving part in a radial direction.

17. The polyaxial bone anchoring device of claim 1, wherein when the head, the pressure member, and the locking member are in the receiving part and the locking member is at the first position, a first length of an inner wall of the receiving part extends from an axial position corresponding to one end of the elastically deformable portion to an axial position corresponding to an opposite end of the elastically deformable portion, and a greatest diameter of the elastically deformable portion is less than a smallest diameter of the first length of the inner wall.

18. The polyaxial bone anchoring device of claim 1, wherein the elastically deformable portion is formed by a slit in the one of the sidewalls that extends downwardly from the top end of the pressure member.

19. The polyaxial bone anchoring device of claim 1, wherein the elastically deformable portion is formed by a notch that extends radially inwardly from an outer surface of the one of the sidewalls.

* * * * *

UNITED STATES PATENT AND TRADEMARK OFFICE
CERTIFICATE OF CORRECTION

PATENT NO.       : 10,010,353 B2
APPLICATION NO.  : 15/299390
DATED            : July 3, 2018
INVENTOR(S)      : Lutz Biedermann et al.

Page 1 of 1

It is certified that error appears in the above-identified patent and that said Letters Patent is hereby corrected as shown below:

In the Claims
Column 8, Line 2, Claim 2      after "portion" insert -- is --

Signed and Sealed this
Thirtieth Day of July, 2019

Andrei Iancu
*Director of the United States Patent and Trademark Office*